United States Patent [19]

Metcalf et al.

[11] 4,147,873
[45] Apr. 3, 1979

[54] α-VINYL DERIVATIVES OF α-AMINO ACIDS

[75] Inventors: Brian W. Metcalf, Strasbourg; Michel Jung, Illkirch Graffenstaden, both of France

[73] Assignee: Merrell Toraude et Compagnie, Strasbourg, France

[21] Appl. No.: 812,050

[22] Filed: Jul. 1, 1977

[51] Int. Cl.² .................. C07D 211/60; C07D 207/16; C07C 101/28

[52] U.S. Cl. ..................................... 546/221; 560/171; 562/426; 562/448; 562/450; 562/565; 562/571; 424/319; 260/326.45; 260/558 A; 260/559 A; 260/561 A; 542/416; 546/243; 560/16; 560/39; 560/41; 560/159; 560/160; 560/169

[58] Field of Search ................. 260/293.86, 326.5 FL, 260/558 A, 559 A, 561 A, 326.45, 293.76; 560/39, 41, 169, 171, 159, 160; 562/565, 571, 448, 450

[56] References Cited

U.S. PATENT DOCUMENTS

| | | | |
|---|---|---|---|
| 2,929,836 | 3/1960 | Carrara | 560/41 |
| 3,197,477 | 7/1965 | Gubitz | 548/308 |
| 3,946,074 | 3/1976 | Abramitis | 260/561 A |
| 3,960,927 | 6/1976 | Metcalf et al. | 424/274 |

FOREIGN PATENT DOCUMENTS 479500 12/1951 Canada ............................... 260/293.86

OTHER PUBLICATIONS

March, J., Advanced Organic Chemistry, McGraw Hill, New York, 1968, p. 335.

Primary Examiner—Natalie Trousof
Assistant Examiner—Richard A. Schwartz
Attorney, Agent, or Firm—L. Ruth Hattan; Eugene O. Retter; George W. Rauchfuss, Jr.

[57] ABSTRACT

Novel vinyl derivatives of α-amino acids of the following general structure:

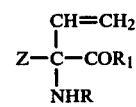

wherein R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

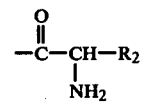

wherein $R_2$ is hydrogen, a straight or branched lower alkyl group of from 1 to 4 carbon atoms, benzyl or p-hydroxybenzyl; Z is $R_1OCCH=CH-$ or $R_1OC(CH_2)_n-$ wherein n is an integer of from 1 to 3; each $R_1$ is the same and is hydroxy, a straight or branched alkoxy group of from 1 to 8 carbon atoms, $-NR_3R_4$ wherein each of $R_3$ and $R_4$ is hydrogen or a lower alkyl group of from 1 to 4 carbon atoms and can be the same or different, or

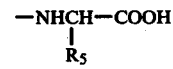

wherein $R_5$ is hydrogen, a straight or branched lower alkyl group of from 1 to 4 carbon atoms, benzyl or p-hydroxybenzyl; and the lactams thereof when Z is $R_1OC(CH_2)_n-$ and n is 2 or 3; and pharmaceutically acceptable salts and individual optical isomers thereof.

9 Claims, No Drawings

α-VINYL DERIVATIVES OF α-AMINO ACIDS

FIELD OF INVENTION

This invention relates to novel α-vinylamino acid derivatives which are useful pharmacological agents and useful as intermediates.

SUMMARY OF INVENTION

Compounds of the following general Formula I are novel derivatives useful as antibacterial agents, as central nervous system excitatory agents, as intermediates for the preparation of useful cephalosporin derivatives and when R is $R_1OC(CH_2)_n-$ useful as intermediates for preparing the corresponding α-acetylene derivatives.

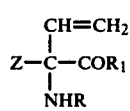

Formula I

In the above general Formula I Z is $R_1OCCH=CH-$ or $R_1OC(CH_2)_n-$ wherein n is an integer of from 1 to 3; each $R_1$ is the same and is hydroxy, a straight or branched alkoxy group of from 1 to 8 carbon atoms, $-NR_3R_4$ wherein each of $R_3$ and $R_4$ is hydrogen or a straight or branched lower alkyl group of from 1 to 4 carbon atoms and can be the same or different, or

wherein $R_5$ is hydrogen, a straight or branched lower alkyl group of from 1 to 4 carbon atoms, benzyl or p-hydroxybenzyl; and R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

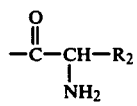

wherein $R_2$ is hydrogen, a straight or branched lower alkyl group of from 1 to 4 carbon atoms, benzyl or p-hydroxybenzyl. The lactams of the compounds of general Formula I wherein Z is $R_1OC(CH_2)_n-$ wherein n is 2 or 3, and R is hydrogen are also included within the scope of the present invention and are represented by the following general Formula II:

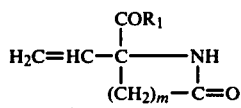

Formula II

In the above general Formula II m is the integer 2 or 3, and $R_1$ has the meaning defined in general Formula I.

Pharmaceutically acceptable salts of the compounds of general Formulas I and II and individual optical isomers of the compounds of general Formula I are included within the scope of the present invention.

DETAILED DESCRIPTION OF INVENTION

As used in general Formula I the term alkylcarbonyl is taken to mean the group

wherein the alkyl moiety has from 1 to 4 carbon atoms and is straight or branched, for example, methyl, ethyl, n-propyl, isopropyl, n-butyl, isobutyl and tert-butyl.

As used in general Formula I the term alkoxycarbonyl is taken to mean the group

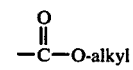

wherein the alkoxy moiety, that is, —O-alkyl, has from 1 to 4 carbon atoms and is straight or branched, for example, methoxy, ethoxy, n-propoxy, isopropoxy, n-butoxy, and tert-butoxy.

Illustrative examples of straight or branched alkyl groups having from 1 to 4 carbon atoms as used in general Formula I are methyl, ethyl, n-propyl, n-butyl, isopropyl and tert-butyl.

Illustrative examples of alkoxy groups having from 1 to 8 carbon atoms as used in general Formula I are methoxy, ethoxy, propoxy, butoxy, pentyloxy, and octyloxy.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids, such as, methane sulfonic, salicylic, maleic, malonic, tartaric, citric and ascorbic acids; and non-toxic salts formed with inorganic or organic bases such as those of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylamino-ethanol, ethanolamine and piperazine. The salts are prepared by conventional means.

Preferred compounds of the present invention are those of general Formula I wherein each $R_1$ is hydroxy and within these preferred compounds those wherein R is hydrogen are more preferred. When Z represents $R_1OC(CH_2)_n-$ compounds wherein n is the integer 2 are more preferred. The most preferred compounds of this invention are those wherein Z is $R_1OCCH=CH-$.

Illustrative examples of compounds of the present invention are the following:
2-amino-2-vinylsuccinic acid,
2-vinylglutamic acid,
2-amino-2-vinyladipic acid,
2-vinyl-3,4-dehydroglutamic acid,
2-amino-2-vinylsuccinic acid dimethyl ester,
2-vinylglutamic acid dimethyl ester,
2-amino-2-vinyladipic acid dimethyl ester,
2-vinyl-3,4-dehydroglutamic acid dimethyl ester,
2-amino-2-vinylsuccinic acid di-n-propyl ester,
2-vinylglutamic acid diethyl ester,
2-amino-2-vinyladipic acid di-isopentyl ester,
2-vinyl-3,4-dehydroglutamic acid di-n-butyl ester,
2-vinylglutamic acid di-tert-butyl ester,
2-(1-oxoethyl)amino-2-vinylsuccinic acid dihexyl ester, 2-(1-oxobutyl)amino-2-vinyladipic acid dioctyl ester,
2-(1-oxoethyl)amino-2-vinylglutaric acid,
2-(1-oxopropyl)amino-2-vinyl-3,4-dehydroglutaric acid,
2-(1-oxopropyl)amino-2-vinylglutaric acid dimethyl ester,
2-(1-oxoethyl)amino-2-vinyl-3,4-dehydroglutaric acid diethyl ester,
2-amino-2-vinylsuccinic acid diamide,
2-amino-2-vinylglutaric acid diamide,
2-amino-2-vinyladipic acid diamide,
2-(1-oxopentyl)amino-2-vinylsuccinic acid diamide,
2-(1-oxoethyl)amino-2-vinylglutaric acid diamide,
2-ethoxycarbonylamino-2-vinyladipic acid diamide,
2-methoxycarbonylamino-2-vinyl-3,4-dehydroglutaric acid diamide,
N,N'-dimethyl-2-amino-2-vinylglutaric acid diamide,
N,N,N',N'-tetraethyl-2-amino-2-vinylglutaric acid diamide,
N,N'-dimethyl-2-amino-2-vinyl-3,4-dehydroglutaric acid diamide,
N,N,N',N'-tetra-n-butyl-2-(1-oxopropyl)amino-2-vinyladipic acid diamide,
N,N'-dimethyl-2-propoxycarbonylamino-2-vinylsuccinic acid diamide,
N,N'-(2-amino-1,5-dioxo-2-vinyl)pentylene bisaminoacetic acid,
N,N'-(2-amino-1,4-dioxo-2-vinyl)butylene bis-(α-methyl)aminoacetic acid, and
2-acetylene 2-(1-oxoethyl-2-vinyl)aminoglutaric acid.

The compounds of this invention wherein $R_1$ of the carboxy group proximal to the vinyl group is hydroxy are useful as intermediates for the preparation of cephalosporin derivatives of the following general Formula III which are useful as antibacterial agents.

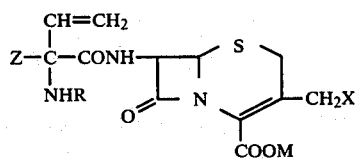

Formula III

In the above general Formula III Z and R have the meanings defined in general Formula I; M is hydrogen or a negative charge; and X is hydrogen or acetoxy.

The compounds of general Formula III and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formula III and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula III, salts and isomers thereof may be incorporated into creams or ointments.

Illustrative examples of bacteria against which the compounds of general Formula III and the pharmaceutically acceptable salts and individual optical isomers thereof are active are *Staphylococcus aureus, Salmonella schotmuehleri, Klebsiella pneumoniae, Diplococcus pneumoniae* and *Streptococcus pyogenes*.

Illustrative pharmaceutically acceptable non-toxic inorganic acid addition salts of the compounds of general Formula III are mineral acid addition salts, for example, hydrogen chloride, hydrogen bromide, sulfates, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of compounds of general Formula III are 7-[[2-amino-4-carboxy-2-vinylbutyryl]amino]-3-acetyloxymethyl-8-oxo-5-thia-1-azabicyclo[4.2.0]oct-2-ene-2-carboxylic acid, 7-[[2-amino-4-methoxy-4-oxo-2-vinylbutyryl]-amino]-3-acetyloxymethyl-8-oxo-5-thia-1-azabicyclo[4.2.0]oct-2-ene-2-carboxylic acid and 7-[[2-amino-5-carboxy-2-vinylvaleryl]amino]-3-acetyloxymethyl-8-oxo-5-thia-1-azabicyclo[4.2.0]oct-2-ene-2-carboxylic acid.

The preparation of the compounds of general Formula III is described hereinbelow.

The compounds of general Formula I are useful as central nervous system excitatory agents, or central nervous system stimulants, and antibacterial agents, or microbicides. The compounds of general Formula I are also irreversible inhibitors of glutamic acid decarboxylase the enzyme which catalyzes in vivo the conversion of glutamic acid to γ-aminobutyric acid. As microbicides the compounds of general Formula I are useful in the control of microorganisms such as *E. coli* and other microorganisms which contain glutamic acid decarboxylase.

The utility of the compounds as irreversible inhibitors of glutamic acid decarboxylase may be demonstrated as follows. Compounds of general Formula I are administered to rats or mice as an aqueous solution or suspension orally or parenterally. At various time intervals the animals are decapitated and the brains homogenized in a phosphate buffer. Glutamic acid decarboxylase activity is measured in the homogenates by the general procedure described by M. J. Jung et al., J. Neurochem. 28, 717-723 (1977).

As irreversible inhibitors of glutamic acid decarboxylase the compounds of general Formula I provide a means of studying the physiological role of γ-aminobutyric acid.

As pharmacologically useful agents the compounds can be administered in various manners to the patient being treated to achieve the desired effect. The compounds can be administered alone or in the form of a pharmaceutical preparation orally, parenterally, for example, intravenously, intraperitoneally, or subcutaneously, or topically. The amount of compound administered will vary over a wide range and can be any effective amount. Depending on the patient to be treated, the condition being treated and the mode of administration, the effective amount of compound administered will vary from about 0.1 mg/kg to 250 mg/kg of body weight of the patient per unit dose and preferably will be about 1 mg/kg to about 50 mg/kg of body weight of patient per unit dose. For example, a typical unit dosage form may be a tablet containing from 10 to 300 mg of a compound of Formula I which may be administered to the patient being treated 1 to 4 times daily to achieve the desired effect.

As used herein the term patient is taken to mean warm blooded animals such as mammals, for example, cats, dogs, rats, mice, guinea pigs, sheep, horses, bovine cows, and humans.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases such as lactose, sucrose or corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The compounds of general Formula I wherein Z is $R_1OC(CH_2)_n$—, R is hydrogen, $R_1$ is hydroxy, and n is the integer 1 to 3, are useful as starting materials for the preparation of compounds of the following general Formula IV:

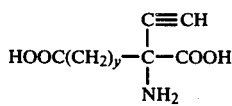

Formula IV wherein y is the integer 1 to 3. The compounds of general Formula IV are useful pharmacological agents. The compounds of general Formula IV are irreversible inhibitors of glutamic acid decarboxylase rendering said compounds useful as central nervous system excitatory agents, or central nervous systems stimulants, and antibacterial agents or microbicides useful in the control of microorganisms such as E. coli.

The compounds of general Formula IV can be administered in the same manner as described herein for the compounds of general Formula I.

In preparing the compounds of Formula IV, 1 equivalent of a compound of Formula I wherein Z is $R_1OC(CH_2)_n$— wherein n is an integer of from 1 to 3, R is hydrogen and $R_1$ is hydroxy in formic acid or lower alkanoic acids, such as, acetic acid is treated with 1 equivalent of bromine at 0° to 30° C. with stirring for about 1 to 24 hours followed by treatment with a strong base in liquid ammonia for about 15 to 30 hours at about 0° to 25° C. Suitable strong bases which may be employed in this reaction are, for example, lithium dialkylamide, such as, lithium diisopropylamide, tert-potassium butylate or sodium amide.

The compounds of general Formula I wherein R is hydrogen and $R_1$ is hydroxy are prepared by treating iminobenzylmethionine lower alkyl ester in a solvent, such as, benzene, dimethylsulfoxide, tetrahydrofuran, diethylether, dioxane, or other ethers with a base, such as, sodium hydride, alkyl amides or potassium tert-butoxide followed by alkylation with a lower alkyl, for example, methyl β-chloroacrylate, when Z is $R_1OCCH=CH$— and $R_1$ is hydroxy, or with lower alkyl bromoacetate, lower alkyl acrylate or spiro-(2,5)-5,7-dioxa-6,6-dimethyloctan-4,8-dione when Z is $R_1OC(CH_2)_n$— wherein R is hydroxy and n varies from 1 to 3 respectively, treating the alkylated derivative with m-chloroperbenzoic acid in ethers, such as, diethyl ether, tetrahydrofuran or dioxane, dichloromethane or chloroform for about 1 to 12 hours at about −70° C. to 25° C. followed by thermolysis by heating to about 100° to 140° C. for about 1 to 12 hours in a solvent such as toluene, xylene, nitrobenzene or a halobenzene, for example, chlorobenzene and subsequently hydrolyzing using acid, for example hydrochloric. The thus obtained salts can be converted to the free base when desired by treatment with a base, for example, aniline, ammonia, one equivalent of sodium or potassium alkoxide or triethylamine. In the above reaction generally equimolar amounts of the iminobenzylmethionine ester, base and alkylating reagent are employed. However, when the alkylating reagent employed is a lower alkyl acrylate a catalytic amount of base may be employed using as a solvent a lower alcohol, for example, methanol or ethanol.

The alkylating reagents employed in the above reaction are commercially available, known in the art or may be obtained by procedures generally known in the art.

The iminobenzylmethionine lower alkyl esters employed in the above reactions are obtained by treating methionine with a lower alcohol, such as, methanol or ethanol saturated with HCl gas at about 25° C. for about 10 to 20 hours to give the ester hydrochloride which is treated with a base such as triethylamine followed by treatment with benzaldehyde.

Alternatively the compounds of general Formula I wherein Z is $R_1OC(CH_2)_n$— wherein n is 2, $R_1$ is hydroxy and R is hydrogen may be prepared by treating one equivalent of iminobenzylmethionine lower alkyl ester in a lower alcoholic solvent, such as, methanol, ethanol or isopropyl alcohol with a catalytic amount of a base, such as, Triton B, sodium alkoxides, for example, sodium methoxide or tertiary amines such as triethylamine or pyridine followed by treatment with one equivalent of a lower alkyl acrylate, for example, methyl acrylate, in an aprotic solvent, such as, benzene, toluene, ethers, tetrahydrofuran, dimethylsulfoxide, or hexamethylphosphortriamide at about −120° to 25° C., preferably about −70° C. for from ½ hour to 24 hours to give the amine protected lower alkyl ester of 6-methylthio-4-amino-4-carbalkoxyhexanoic acid which is hydrolyzed in a lower alcoholic solvent such as, methanol, ethanol or isopropyl alcohol using a mineral acid, such as hydrochloric acid followed by treatment with base, such as, aqueous sodium or potassium hydroxide, sodium or lithium alkoxides, triethylamine or pyridine or using hydrazine, phenylhydrazine or hydroxylamine followed by heating from about 80° to 130° C. for about 1 to 5 hours to form 5-carbalkoxy-5-methylthioethyl-2-pyrrolidone. The pyrrolidone is treated with m-chloroperbenzoic acid in ethers, such as diethyl ether, tetrahydrofuran or dioxane, dichloromethane or chloroform for about 1 to 12 hours at about −70° to 25° C. or treated with sodium m-periodate in a lower alcoholic solvent, such as, methanol or ethanol and water for about 1 to 10 hours at about 0° to 25° C. followed by thermolysis by heating to about 100° to 140° C. for about 1 to 12 hours in a solvent such as, toluene, xylene, nitrobenzene or a halobenzene, for example, chlorobenzene and subsequently hydrolyzing using acid for example hydrochloric acid. The thus obtained salts can be converted to the free base when desired by treatment, for example, with aniline, ammonia, one equivalent of sodium or potassium alkoxide or triethylamine.

Alternatively, in the above reaction the final hydrolysis step may be omitted isolating the lactam corresponding to the compounds of general Formula II wherein R is a lower alkoxy group and m is the integer 2.

The compounds of this invention wherein each $R_1$ is a straight or branched alkoxy group of from 1 to 8 carbon atoms are prepared from the corresponding derivatives wherein $R_1$ is hydroxy by reaction with an alcohol of the formula $R_6OH$, wherein $R_6$ is a straight or branched alkyl group of 1 to 8 carbon atoms, saturated with HCl gas at about 25° C. for from about 12 to 36 hours.

The compounds of general Formula I wherein each $R_1$ is a straight or branched alkoxy group of from 1 to 8 carbon atoms may also be prepared by converting the corresponding compound wherein each $R_1$ is hydroxy to the acid halide by, for example, treatment with thionyl chloride, followed by alcoholysis with an alcohol of the formula $R_6OH$ as defined above by procedures generally known in the art.

The compounds of Formula I wherein each $R_1$ is $NR_3R_4$ and each of $R_3$ and $R_4$ is hydrogen or a straight or branched lower alkyl group of 1 to 4 carbon atoms are prepared by an acylation reaction of an acid halide, for example, an acid chloride, of the corresponding compound wherein each $R_1$ is hydroxy and R has the meaning defined in Formula I with the proviso that any free amino group is suitably protected with groups, such as, carbobenzyloxy or tert-butoxycarbonyl, with an excess of an appropriate amine which may be represented as $NHR_3R_4$. The reaction is carried out in methylene chloride, chloroform, dimethylformamide, ethers, such as tetrahydrofuran or dioxane, or benzene at about 25° C. for about 1 to 4 hours. Suitable amines are ammonia, or a compound which is a potential source of ammonia, for example, hexamethylenetetramine; primary amines, for example, methylamine, ethylamine or n-propylamine; and secondary amines, for example, dimethylamine, diethylamine or di-n-butylamine. Following the acylation reaction the protecting groups are removed by treatment with acid, for example, trifluoroacetic acid or hydrogen bromide in dioxane.

The compounds of general Formula I wherein each $R_1$ is

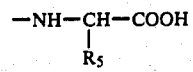

are prepared by reacting the corresponding derivative wherein each $R_1$ is hydroxy or a functional derivative thereof, such as an acid anhydride and R has the meaning defined in Formula I with the proviso that any free amino group is protected with a suitable blocking group, such as benzyloxycarbonyl, tert-butoxycarbonyl, with a compound of the formula

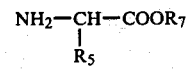

wherein $R_5$ has the meaning defined in general Formula I and $R_7$ is a lower alkyl group, for example, methyl or ethyl in an ether solution, such as, tetrahydrofuran or dioxane at 0° to about 50° C. for about 1 to 24 hours, with the proviso that when the free acid is employed the reaction is carried out using a dehydrating agent such as dicyclohexylcarbodiimide. The protecting groups are removed by acid hydrolysis with, for example, trifluoroacetic acid or hydrogen bromide in dioxane for about 1 to 20 hours.

The compound of general Formula I wherein R is alkylcarbonyl wherein the alkyl moiety is straight or branched and has from 1 to 4 carbon atoms are prepared by treating the corresponding derivative wherein R is hydrogen and $R_1$ is hydroxy with an acid halide of the formula

wherein halo is a halogen atom, for example, chlorine or bromine and $R_8$ is a straight or branched alkyl group having from 1 to 4 carbon atoms or an appropriate acid anhydride in water in the presence of a base such as sodium hydroxide or sodium borate at a temperature of from 0° to about 25° C. for from ½ hour to about 6 hours. These compounds may also be prepared from the ester derivative, that is, compounds of general Formula I wherein R is hydrogen and each $R_1$ is an alkoxy group of from 1 to 8 carbon atoms by treatment with the acid halide,

described above, or an appropriate acid anhydride in water, methylene chloride, chloroform or dimethyl acetamide in the presence of a base such as sodium hydroxide, potassium hydroxide or excess triethylamine at a temperature of from 0° to about 25° C. for from ½ hour to about 24 hours.

The compounds of general Formula I wherein R is alkoxycarbonyl wherein the alkoxy moiety is straight or branched and has from 1 to 4 carbon atoms are prepared by treating the corresponding derivative wherein R is hydrogen and each $R_1$ is hydroxy with a halo alkylformate of the formula

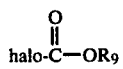

wherein halo is a halogen atom such as chlorine or bromine and $R_9$ is a straight or branched alkyl group having from 1 to 4 carbon atoms in water in the presence of a base such as sodium hydroxide or sodium borate at a temperature of from 0° to about 25° C. for from ½ hour to about 6 hours.

The compounds of general Formula I wherein R is

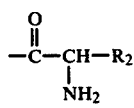

wherein $R_2$ is hydrogen, a straight or branched lower alkyl group of from 1 to 4 carbon atoms, benzyl or p-hydroxybenzyl are prepared by treating the corresponding derivative wherein R is hydrogen and $R_1$ is a straight or branched alkoxy group of from 1 to 8 carbon atoms with an acid of the formula

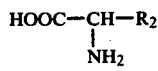

or an anhydride thereof wherein $R_2$ has the meaning defined above and the amino group is protected with a suitable blocking group, such as, benzyloxycarbonyl or tert-butoxycarbonyl in an ether, such as, tetrahydrofuran or dioxane, methylene chloride or chloroform at a temperature of from 0° to about 35° C. for about 1 to 12 hours and in the presence of a dehydrating agent such as dicyclohexyl carbodiimide when the free acid is employed followed by base and acid hydrolysis with, for example, trifluoroacetic acid or hydrogen bromide in dioxane to remove the protecting groups.

The lactams of this invention, that is, compounds of general Formula II, are prepared by heating a diester derivative of the corresponding amino acid of the structure

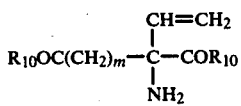

wherein m is the integer 2 or 3, and $R_{10}$ is a straight or branched alkoxy group of from 1 to 8 carbon atoms in a lower alcohol, such as, ethanol or 2-methoxyethanol for about 1 to 24 hours at a temperature of from about 80° to about 120° C.

As set forth hereinabove compounds of general Formula I are useful as intermediates for the preparation of useful cephalosporin derivatives as described by general Formula III. The compounds of general Formula III wherein R is hydrogen and $R_1$ is hydroxy are prepared by coupling 7-aminocephalosporanic acid or a derivative thereof having the formula

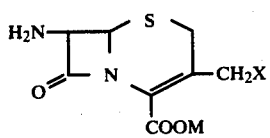

wherein X and M have the meanings defined in general Formula III with an acid of the formula

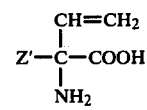

Formula VI or a functional derivative thereof, such as, the acid chloride or an acid anhydride in the presence of a dehydrating agent such as dicyclohexyl carbodiimide when the free acid is employed wherein Z' is

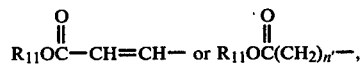

wherein $R_{11}$ is benzyl; n' is an integer of from 1 to 3; and the amino group is protected by suitable blocking groups, for example, tert-butoxycarbonyl followed by acid hydrolysis to remove the amino protecting groups and the benzyl ether resulting in a carboxy derivative.

The coupling reaction is generally carried out in a solvent, such as, ethyl acetate, dioxane, chloroform, or tetrahydrofuran in the presence of a base, such as, alkaline bicarbonate. The temperature of the reaction may vary from about −10° to 100° C., and the reaction time may vary from about ½ hour to 10 hours. The cephalosporin products are isolated by conventional procedures.

The acids of Formula VI are prepared by procedures generally known in the art. For example, the compounds of Formula VI wherein $R_{11}$ is benzyl may be prepared by selective hydrolysis of the corresponding di-carboxylic acid ester derivative by aqueous copper sulfate with isolation of the monoester by the general procedure described by R. L. Prestidge, et al., J. Org. Chem. 40, 3287 (1975).

The compounds of general Formula III wherein R is other than hydrogen and $R_1$ is other than hydroxy are prepared from the corresponding derivatives wherein R is hydrogen and $R_1$ is hydroxy by the general procedures set forth hereinabove for the compounds of general Formula I wherein R is other than hydrogen and $R_1$ is hydroxy. To prepare compounds of general Formula III wherein M is hydrogen and $R_1$ is other than hydroxy protection of the cephalosporin acid group by, for example, conversion to the tert-butyl ester prior to coupling may be desirable.

EXAMPLE 1

2-Vinylglutamic acid

A solution of 2.5 g (10 mM) of iminobenzylmethionine methyl ester in 15 ml of methanol at 25° C. is treated with a catalytic amount of Triton B followed by 860 mg (10 mM) of methyl acrylate. The mixture is stirred overnight at 25° C. then the solvent is evaporated leaving a residue which is dissolved in ether, washed well with water, dried and evaporated giving methyl 4-carbomethoxy-4-iminobenzyl-6-methylthiohexanoate (2.5 g) which is stirred with 20 ml of 0.5 M HCl at 25° C. for 3 hours. The mixture is then washed with methylene chloride, evaporated and the residue taken up in 2-methoxyethanol containing 250 mg of sodium. The mixture is refluxed for 1 hour, then the solvent is evaporated. The resulting residue is triturated with ether, filtered, the filtrate dried and evaporated to give 5-carbomethoxy-5-methylthioethyl-2-pyrrolidone which is purified by chromatography on silicic acid, eluting with 2% methanol-chloroform. A solution of 2.0 g (10 mM) of the methylthioethyl substituted pyrrolidone in 15 ml of dichloromethane at 0° C. is treated with 1.72 g (10 mM) of m-chloroperbenzoic acid. After 12 hours at 0° C. the precipitate is filtered off and the filtrate evaporated. The resulting residue is taken up in 50 ml xylene and heated under reflux overnight afterwhich the solvent is evaporated giving 5-carbomethoxy-5-vinyl-2-pyrrolidone which is purified by chromatography on silicic acid. The vinyl pyrrolidone (1 g, 6.0 mM) is heated with 20 ml of 6 N hydrochloric acid for 1 hour, then the mixture is concentrated to dryness. The residue is dissolved in the minimum volume of ethanol and 560 mg of aniline is added. The mixture is maintained at 0° C. overnight and the resulting precipitate filtered off to give 2-vinylglutamic acid.

EXAMPLE 2

2-Vinyl-3,4-dehydroglutamic acid

A solution of 2.5 g (10 mM) of iminobenzylmethionine methyl ester in 5 ml of tetrahydrofuran is added to a solution of lithium diisopropylamide (10 mM) in 30 ml of tetrahydrofuran at −70° C. After 5 minutes methyl β-chloroacrylate (1.2 g, 10 mM) is added, and the solution allowed to warm to 25° C. Water is added and the mixture extracted with ether. The ether solution is washed with water, dried and concentrated to afford methyl 4-carbomethoxy-4-iminobenzyl-6-methylthiohex-2-enoate. The methylthio substituted ester (3.5 g, 10 mM) in 10 ml of dichloromethane is cooled to −70° C. then treated with 1.7 g, 10 mM of m-chloroperbenzoic acid. The mixture is maintained at 0° C. overnight then filtered. The filtrate is washed with aqueous bicarbonate then evaporated leaving a residue which is taken up in m-xylene (30 ml) and heated overnight at reflux after which the solvent is evaporated. The residue is treated with 20 ml of 6 N HCl for 4 hours at 50° C. then washed with dichloromethane. The aqueous phase is concentrated to dryness to give the hydrochloride salt of 2-vinyl-3,4-dehydroglutamic acid which is converted to the free base by dissolving the salt in the minimum amount of ethanol and 930 mg (10 mM) of aniline added. The solution is allowed to stand overnight at 0° C. and the resulting precipitate collected to give 2-vinyl-3,4-dehydroglutamic acid.

EXAMPLE 3

7-[[2-Amino-4-carboxy-2-vinylbutyryl]amino]-3-acetyloxymethyl-8-oxo-5-thia-1-azabicyclo[4.2.0]oct-2-ene-2-carboxylic acid A mixture of 1 gram of 3-acetyloxy-7-amino-8-oxo-5-thia-1-azabicyclo[4.2.0]oct-2-ene-2-carboxylic acid and 1 g of 4-benzyloxycarbonyl-2-vinylglutamic acid chloride wherein the free amino group is protected with tert-butoxycarbonyl in 50 ml of ethyl acetate is refluxed for 2 hours after which the solvent is removed leaving a residue which is treated with mild acid and chromatographed on silica gel using benzene-acetone as the eluant to give 7-[[2-amino-4-carboxy-2-vinylbutyryl]amino]-3-acetyloxymethyl-8-oxo-5-thia-1-azabicyclo[4.2.0]oct-2-ene-2-carboxylic acid.

The following examples are illustrative of pharmaceutical preparations of compounds of general Formula I.

EXAMPLE 4

An illustrative composition for hard gelatin capsules is as follows:

| (a) | 2-vinylglutamic acid | 10 mg |
|---|---|---|
| (b) | talc | 5 mg |
| (c) | lactose | 100 mg |

The formulation is prepared by passing the dry powders of (a) and (b) through a fine mesh screen and mixing them well. The powder is then filled into hard gelatin capsules at a net fill of 115 mg per capsule.

EXAMPLE 5

An illustrative composition for tablets is as follows:

| (a) | 2-amino-2-vinyl-3,4-dehydroglutamic acid | 5 mg |
|---|---|---|
| (b) | starch | 43 mg |
| (c) | lactose | 60 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 6

An illustrative composition for an injectable suspension is the following 1 ml ampul for an intramuscular injection.

| | | Weight percent |
|---|---|---|
| (a) | 2-amino-2-vinylsuccinic acid | 1.0 |
| (b) | polyvinylpyrrolidone | 0.5 |
| (c) | lecithin | 0.25 |
| (d) | water for injection to make | 100.0 |

The materials (a)–(d) are mixed, homogenized, and filled into 1 ml ampuls which are sealed and autoclaved 20 minutes at 121° C. Each ampul contains 10 mg per ml of novel compound (a).

EXAMPLE 7

Dimethyl-2-vinylglutamate

2-Vinylglutamic acid (500 mg, 2.9 mM) is added to methanol (40 ml) which is saturated with dry hydrogen chloride. The solution is heated at reflux for 12 hours, then the solvent evaporated to afford dimethyl-2-vinylglutamate.

EXAMPLE 8

N-Acetyl-2-vinylglutamic acid

To a solution of 2-vinylglutamic acid (350 mg, 2 mM) in 5 ml of 1 N sodium hydroxide at 0° C. are added simultaneously from 2 syringes acetyl chloride (160 mg) diluted in dioxane (1 ml) and 2 ml of 1 N sodium hydroxide. After 30 minutes at 0° the solution is acidified by the addition of 3 N hydrochloric acid, then extracted well with dichloromethane. The organic phase is dried and concentrated to afford N-acetyl-2-vinylglutamic acid.

In a similar manner, but with acetyl chloride replaced by ethyl chloroformate (220 mg) N-ethoxycarbonyl-2-vinylglutamic acid is obtained.

EXAMPLE 9

N,N'-Dipropyl-2-amino-2-vinyl-1,5-pentanediamine hydrobromide

To a solution of 2-vinylglutamic acid (350 mg, 2 mM) in 5 ml of 1 N sodium hydroxide at 0° C. are added simultaneously from two syringes benzyl chloroformate (340 mg, 2 mM) in dioxane (1 ml) and 2 ml of 1 N sodium hydroxide. After 30 minutes at 0° C. the solution is acidified by the addition of 6 N hydrochloric acid, then extracted well with dichloromethane. The organic phase is dried and concentrated to afford N-(benzyloxycarbonyl)-2-vinyl-3-glutamic acid. This was dissolved in dichloromethane (15 ml) and treated with thionyl chloride (230 mg) at 25° C. for one hour. Propylamine (500 mg) is then added and the solution stirred at 25° C. for one hour, then washed with water, dried and concentrated. The residue is treated with 6 ml of a solution of dioxane containing hydrogen bromide (40% w/w) and allowed to stand for 30 minutes at 25° C. Ether (50 ml) is then added and the resulting precipitate collected to afford N,N'-dipropyl-2-amino-2-vinyl-1,5-pentanediamide hydrobromide.

EXAMPLE 10

5-Amino-2,10-dimethyl-4,8-dioxo-5-vinyl-3,9-diazaundecanedioic acid

To 2-(benzyloxycarbonyl)amino-2-vinylglutaric acid (305 mg, 1 mM) in methylene chloride (15 ml) is added triethylamine (205 mg, 2 mM) followed by ethyl chloroformate (218 mg, 2 mM). The solution is stirred for one hour at 25° C., then alanine methyl ester (206 mg, 2 mM) in methylene chloride (5 ml) is added. This solution is kept overnight at 25° C., washed with water, dried and evaporated to dryness. The residue is treated with 5 ml of a 40% (w/w) solution of hydrogen bromide in dioxane at 25° C. for 30 minutes. Ether (50 ml) is then added and the precipitate collected. This is then treated with 20 ml of a 1 N sodium hydroxide solution overnight at 25° C., the pH adjusted to 6.5, and applied to an Amberlite 120 H+ resin. Elution with 2 N ammonium hydroxide afforded 5-amino-2,10-dimethyl-4,8-dioxo-5-vinyl-3,9-diazaundecanedioic acid.

EXAMPLE 11

5-Methoxycarbonyl-5-vinyl-2-vinylglutamate-2-pyrrolidone

Dimethyl 2-vinylglutamate hydrochloride (570 mg, 2 mM), is treated with saturated aqueous sodium carbonate (20 ml) and the resulting mixture extracted with dichloromethane. The organic phase is dried and concentrated to afford the free base which is dissolved in 2-methoxyethanol (20 ml) and heated under reflux for 2 hours. The solvent is then removed in vacuo to afford 5-methoxycarbonyl-5-vinyl-2-pyrrolidone.

5-Carboxy-4-vinyl-2-pyrrolidone is prepared by treatment of the lactam ester (360 mg, 2 mM) with aqueous sodium hydrochloride (10 ml of a 1 N solution) at room temperature for 3 hours. The solution is then acidified (2 N hydrochloric acid) and extracted exhaustively with chloroform. The organic phase is dried and evaporated to afford 5-carboxy-5-vinyl-2-pyrrolidone.

EXAMPLE 12

N-(2-Aminopropylcarbonyl)-2-vinylglutamic acid

Dimethyl 2-vinylglutamate (200 mg, 1 mM) in methylene chloride (4 ml) is treated with N-carbobenzoxy alanine (200 mg, 1 mM) and N,N'-dicyclohexylcarbodiimide (206 mg, 1 mM) overnight at 25° C. The mixture is then cooled to 0° C. and the precipitated dicyclohexyl urea filtered off. The filtrate is diluted with methylene chloride, washed with water, bicarbonate, dilute hydrochloric acid, then dried and concentrated. The residue is treated with ethanol (5 ml) and 5 ml of a 40% (w/w) solution of hydrogen bromide in dioxane for 30 minutes at 25° C. Ether (50 ml) is then added and the resulting precipitate collected which is treated with 1 N sodium hydroxide (15 ml) overnight at 25° C. The pH of the solution is adjusted to neutral and the product isolated from an Amberlite 120 H+ resin by elution with 2 M ammonium hydroxide affording N-(2-aminopropylcarbonyl)-2-vinylglutamic acid.

When in the procedure of Example 2 an appropriate amount of methyl bromoacetate, methyl acrylate or spiro-(2,5)-5,7-dioxa-6,6-dimethyloctan-4,8-dione is substituted for methyl β-chloroacrylate the following respective products are obtained:
2-amino-2-vinylsuccinic acid,
2-vinylglutamic acid, and
2-amino-2-vinyladipic acid.

We claim:
1. A compound of the formula

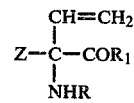

wherein Z is $R_1OCCH=CH-$ or $R_1OC(CH_2)_n-$ wherein n is an integer of from 1 to 3; each $R_1$ is the same and is hydroxy, a straight or branched alkoxy group of from 1 to 8 carbon atoms, $-NR_3R_4$ wherein each of $R_3$ and $R_4$ is hydrogen or a straight or branched lower alkyl group of from 1 to 4 carbon atoms and can be the same or different, or

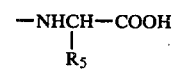

wherein $R_5$ is hydrogen, a straight or branched lower alkyl group of from 1 to 4 carbon atoms, benzyl or p-hydroxybenzyl; and R is hydrogen, alkylcarbonyl wherein the alkyl moiety has from 2 to 4 carbon atoms and is straight or branched, alkoxycarbonyl wherein the alkoxy moiety has from 1 to 4 carbon atoms and is straight or branched or

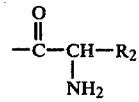

wherein $R_2$ is hydrogen, a straight or branched lower alkyl group of from 1 to 4 carbon atoms, benzyl or p-hydroxybenzyl; and the lactams of said compounds wherein Z is $R_1OC(CH_2)_n-$ wherein n is the integer 2 or 3 and R is hydrogen; and pharmaceutically acceptable salts and individual optical isomers thereof.

2. A compound of claim 1 wherein each $R_1$ is hydroxy or a straight or branched alkoxy group of from 1 to 8 carbon atoms.

3. A compound of claim 1 wherein R is hydrogen or alkylcarbonyl wherein the alkyl moiety has from 1 to 4 carbon atoms and is straight or branched.

4. A compound of claim 1 wherein $R_1$ is hydroxy or a straight or branched alkoxy group of from 1 to 8 carbon atoms.

5. A compound of claim 1 wherein R is hydrogen and $R_1$ is hydroxy.

6. A compound of claim 1 wherein Z is $R_1OCCH=CH$.

7. A compound of claim 1 which is 2-vinylglutamic acid.

8. A compound of claim 1 which is 2-vinyl-3,4-dehydroglutamic acid.

9. A lactam of claim 1 wherein Z is $R_1OC(CH_2)_n-$ and n is the integer 2 or 3 and R is hydrogen having the structure

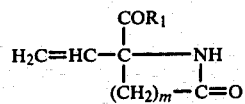

wherein m is the integer 2 or 3 and $R_1$ has the meaning defined in claim 1.

* * * * *